(12) United States Patent
Sano et al.

(10) Patent No.: US 6,280,767 B1
(45) Date of Patent: Aug. 28, 2001

(54) SOFT GELATIN CAPSULE

(75) Inventors: Yasuhiko Sano; Makoto Itoh; Yosimitsu Nakajima; Itsumi Enomoto, all of Fuji (JP)

(73) Assignee: Toaki Capsule Co., Ltd., Fuji (JP)

( * ) Notice: Subject to any disclaimer, the term of this patent is extended or adjusted under 35 U.S.C. 154(b) by 0 days.

(21) Appl. No.: 09/414,863

(22) Filed: Oct. 8, 1999

(30) Foreign Application Priority Data

Oct. 20, 1998 (JP) .................................................. 10-298166

(51) Int. Cl.$^7$ ...................................................... A61K 9/48
(52) U.S. Cl. .......................... 424/456; 424/451; 424/452; 424/454; 514/962
(58) Field of Search .................................... 424/451, 454, 424/452, 456, 455, 453

(56) References Cited

U.S. PATENT DOCUMENTS 4,138,013 * 2/1979 Okajima ................................. 206/528
5,063,057 * 11/1991 Spellman et al. ..................... 424/401
5,270,054 * 12/1993 Bertolini ............................... 424/451
5,641,510 * 6/1997 Clark et al. ........................... 424/451
5,770,225 * 6/1998 Parekh et al. ........................ 424/456

* cited by examiner

Primary Examiner—James M. Spear
(74) Attorney, Agent, or Firm—Oblon, Spivak, McClelland, Maier & Neustadt, P.C.

(57) ABSTRACT

The present invention relates to a chewable soft gelatin capsule and a soft gelatin capsule of the torsional opening type, the capsule having a shell which includes:

(A) gelatin
(B) one or more plasticizers selected from among (b1)–(b3) below, in a total amount of 100–600 parts by weight based on 100 parts by weight of gelatin;
   (b1) glycerin
   (b2) a sugar selected from among D-sorbitol, sucrose, mannitol, fructose, sugar alcohol, and isomerized sugar
   (b3) a glycol selected from propylene glycol and ethylene glycol, and
(C) a water-insoluble cellulose.

13 Claims, 1 Drawing Sheet

SOFT GELATIN CAPSULE

BACKGROUND OF THE INVENTION

1. Field of the Invention

The present invention relates to a soft gelatin capsule which is easy to chew and is not sticky, and which is suitable for encapsulating, for example, pharmaceuticals, food, and health food. Further, the present invention relates to a soft gelatin capsule which is easy to twist open with the fingers, and is suitable for encapsulating, for example, pharmaceuticals, cosmetics, and food.

2. Description of the Background Art

Children and the elderly often experience difficulty in swallowing and ingesting medicines in solid forms, such as tablets, pills, and capsules. Pharmaceuticals in forms which permit easy ingestion and whose active components are rapidly released in the oral cavity are desirable in the event of a medical emergency such as an attack of angina pectoris.

Recently, with diversification of personal preferences in food, texture of food within the mouth is being addressed. For example, nata de coco, a food having a chewy texture, was very popular a short time ago.

Among solid medicines having elasticity, mention may be given of a soft gelatin capsule. In a conventional soft gelatin capsule, ingredients are encapsulated in a gelatin shell which is produced by extending a mixture of gelatin, plasticizer, and water into a thin sheet. Generally, the shell of a soft gelatin capsule is produced by adding, to gelatin, a plasticizer in an amount of 30–40 wt. % with respect to the gelatin; and drying the shell until the water content becomes 5–10 wt. %, so as to prevent the capsule from being deformed or becoming undesirably sticky.

The soft gelatin capsule prepared as described above is hard and tough, because it is designed to dissolve after reaching the intestines so as to release its contents therein. Therefore, the capsule is not easily broken in the mouth by teeth and is not suitable for chewing.

Also, because the conventional soft gelatin capsule is hard and tough as described above, twisting the capsule open by the fingers is difficult in practice, and opening the capsule requires a tool such as scissors. Therefore, the conventional capsule is unsuitable for external-use compositions and cosmetics which are removed from the capsule before use, as well as medicines which are required to be quick-acting.

One measure for further softening a soft gelatin capsule is to increase plasticizer content. This makes a soft gelatin capsule more likely to stick to another soft gelatin capsule or to a container, thereby causing deterioration in storage stability. Thus, increasing plasticizer content is inappropriate in a high-temperature, high-humidity region such as Japan. Also, a soft gelatin capsule of high plasticizer content tends to stick to, for example, the teeth during chewing.

In view of the above-described circumstances, the present inventors conducted earnest studies and found that increasing by several fold the amount of a plasticizer conventionally used for forming a gelatin shell and incorporating insoluble cellulose therein yields a soft gelatin capsule which has a soft, pleasant chewing texture and low stickiness and can be easily and reliably twisted open with the fingers. The present invention has been achieved on the basis of this finding.

SUMMARY OF THE INVENTION

In view of the foregoing, the present invention provides a soft gelatin capsule for chewing which is easily broken in the mouth and which has low stickiness and excellent solubility.

The present invention also provides a soft gelatin capsule which can be easily and reliably opened, without use of any tools such as scissors, by twisting with the fingers, and which has less stickiness and excellent storage stability.

Accordingly, in one aspect of the present invention, there is provided a soft gelatin capsule for chewing, the capsule having a shell which comprises the following components (A), (B), and (C):

(A) gelatin (B) one or more plasticizers selected from among (b1)–(b3) below, in a total amount of 100–600 parts by weight based on 100 parts by weight of gelatin.

(b1) glycerin (b2) a sugar selected from among D-sorbitol, sucrose, mannitol, fructose, sugar alcohol, and isomerized sugar (b3) a glycol selected from propylene glycol and polyethylene glycol, and (C) a water-insoluble cellulose.

In another aspect of the present invention, there is provided a soft gelatin capsule of the torsional opening type having a shell which contains the above-mentioned components (A), (B), and (C).

BRIEF DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which.

DESCRIPTION OF THE PREFERRED EMBODIMENTS

Figure 1:
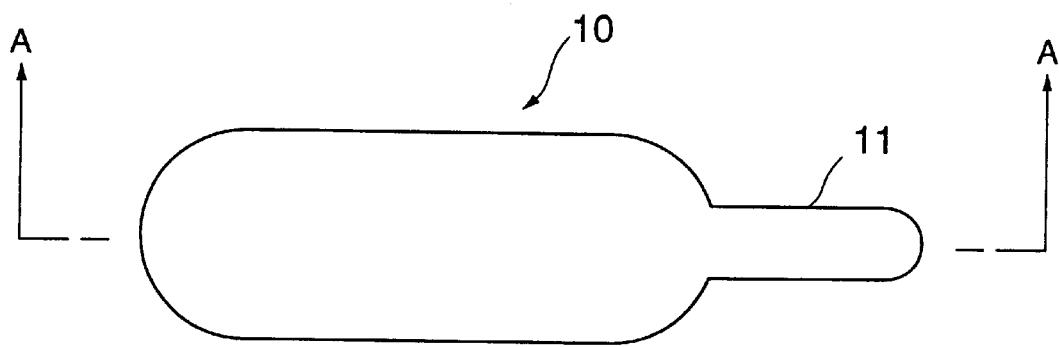
FIG. 1 is a schematic plan view of a soft gelatin capsule of the torsional opening type according to the present invention.

In the present specification, the term "gelatin" refers to gelatin, acidic gelatin, alkaline gelatin, peptide gelatin, low-molecular-weight gelatin, and gelatin derivatives. The soft gelatin capsule of the present invention may contain any of these species of gelatin as ingredient (A) of the shell.

The shell contains as component (B) one or more plasticizers selected from among (b1) glycerin, (b2) a sugar, and (b3) a glycol. When a plurality of plasticizers are contained, preferably, at least (b1) glycerin is contained. More preferably, in consideration of ease of molding, the shell contains, as plasticizers, (b1) glycerin in combination with at least any one of (b2) a sugar and (b3) a glycol.

The shell contains the plasticizer preferably in a total amount of 100–600 parts by weight based on 100 parts by weight of gelatin serving as component (A), more preferably between 150 and 300 parts by weight. Amounts less than 100 parts by weight yield a hard capsule, whereas amounts in excess of 600 parts by weight yield a soft gelatin capsule that is difficult to mold.

When the shell contains glycerin (b1) alone as component (B), glycerin is preferably used in an amount of 100–300 parts by weight, more preferably 120–200 parts by weight, based on 100 parts by weight of gelatin (A).

In the present invention, the shell contains a sugar (b2) selected from among D-sorbitol, sucrose, mannitol, fructose, sugar alcohol, and isomerized sugar. Of these, D-sorbitol, sucrose, and mannitol are preferably chosen, for the purpose of providing a sweet taste upon chewing of the shell. D-sorbitol and mannitol are preferable because of their low stickiness when contained at high concentration. When a sugar is used alone as a plasticizer, the sugar is preferably incorporated in an amount of 100–300 parts by weight, more preferably 120–200 parts by weight, based on 100 parts by weight of gelatin (A).

When glycerin (b1) is used in combination with a sugar (b2), such combination improves compatibility, and thus the concentration of plasticizer can be increased. When glycerin and a sugar are used in combination, glycerin is preferably incorporated in an amount of 50–300 parts by weight, more preferably 50–250 parts by weight, based on 100 parts by weight of gelatin; and the sugar is preferably incorporated in an amount of 30–300 parts by weight, more preferably 50–150 parts by weight, based on 100 parts by weight of gelatin.

In the present invention, the shell contains a glycol (b3) selected from propylene glycol and polyethylene glycol. More preferably, polyethylene glycol which has a weight average molecular weight of 400–4000 is used. Because of the high hygroscopicity of glycol, a soft gelatin capsule produced by use of a glycol becomes difficult to handle. Therefore, incorporation of a glycol in a large amount is not preferable. If glycol alone is used as a plasticizer, the amount of glycol is preferably 100–200 parts by weight, more preferably 120–180 parts by weight, based on 100 parts by weight of gelatin (A).

When glycerin (b1) and a glycol (b3) are used in combination, a very soft gelatin shell can be obtained. When glycerin is used in combination with propylene glycol from (b3), glycerin is preferably incorporated in an amount of 40–200 parts by weight, more preferably 50–120 parts by weight, based on 100 parts by weight of gelatin (A); and propylene glycol is preferably incorporated in an amount of 20–300 parts by weight, more preferably 40–100 parts by weight, based on 100 parts by weight of gelatin (A). When glycerin is used in combination with polyethylene glycol from (b3), glycerin is preferably incorporated in an amount of 50–100 parts by weight, more preferably 60–80 parts by weight, based on 100 parts by weight of gelatin; and polyethylene glycol is preferably incorporated in an amount of 40–200 parts by weight, more preferably 50–100 parts by weight, based on 100 parts by weight of gelatin.

When three plasticizers; that is, glycerin (b1), a sugar (b2), and a glycol (b3), are used in combination, glycerin is preferably incorporated in an amount of 50–200 parts by weight, more preferably 60–150 parts by weight, based on 100 parts by weight of gelatin; the sugar is preferably incorporated in an amount of 30–130 parts by weight, more preferably 40–80 parts by weight, based on 100 parts by weight of gelatin; and the glycol is preferably incorporated in an amount of 20–120 parts by weight, more preferably 50–100 parts by weight, based on 100 parts by weight of gelatin.

Examples of component (C); i.e., water-insoluble cellulose, include crystalline cellulose, ethyl cellulose, low-substitution-degree hydroxypropyl cellulose, and starch. Water-insoluble celluloses are preferably incorporated in an amount of 5–100 parts by weight, more preferably 25–75 parts by weight, based on 100 parts by weight of gelatin (A). Amounts of water-insoluble celluloses less than 5 parts by weight based on 100 parts by weight of gelatin are not preferred, from the viewpoints of poor improvement in suppression of stickiness of a soft gelatin capsule, adhesion of a soft gelatin capsule to another soft gelatin capsule or to a container, and unfavorable sticky texture in the mouth. When water-insoluble celluloses are incorporated in amounts in excess of 100 parts by weight based on 100 parts by weight of gelatin, molding of a soft gelatin capsule becomes difficult.

The shell of the soft gelatin capsule according to the present invention may contain, in addition to components (A)–(C), a coloring agent, a preservative, a disintegrant, a surfactant, a fragrance, a sweetening agent, or a flavoring agent, as needed.

The soft gelatin capsule of the present invention can be produced according to a conventional method of producing a soft gelatin capsule. Briefly, a soft gelatin capsule is produced, for example, by the following method. Components (A), (B) and (C) are dissolved with heat. Water and other arbitrarily selected components are added to the resultant solution, to thereby obtain a composition of a shell. The composition assuming a sheet form is supplied to a soft gelatin capsule manufacturing machine, and deformed against the walls of mold cavities. Simultaneously, ingredients to be encapsulated in the capsule are injected thereto, and the composition is solidified under cooling.

Figure 2:
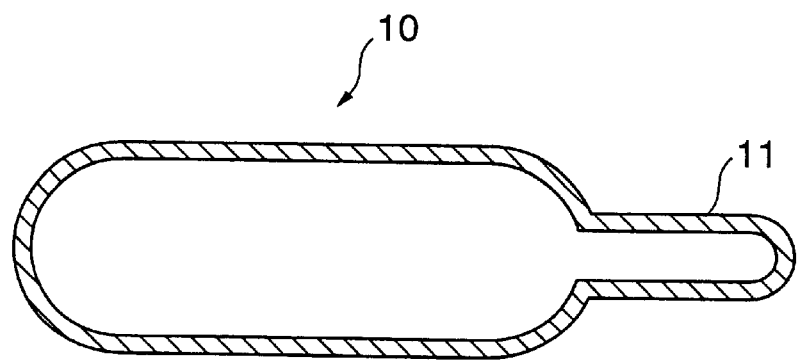
FIG. 2 is a sectional view of the soft gelatin capsule taken along line A—A of FIG. 1.

The soft gelatin capsule can be opened by twisting any parts of the capsule with the fingers, because its shell has the above-described composition. If a narrow rupture portion 11 is provided at an arbitrary portion of the body 10 of the capsule, preferably at the end of the body as shown in FIGS. 1 and 2, the soft gelatin capsule can advantageously be more easily and reliably twisted open with the fingers.

EXAMPLES

The present invention will next be described in detail below by way of examples, which should not be construed as limiting the invention thereto.

Test Example 1

Gelatin sheets were prepared from a variety of gelatin compositions, and the sheets were evaluated in terms of texture, taste, and stickiness in the mouth, and stickiness between sheets.

<Preparation of Gelatin Sheet>

(1) Concentrated glycerin (as specified in the Japanese Pharmacopoeia)(100 g) and a suitable amount of purified water were placed in a 1-liter beaker and mixed. Subsequently, gelatin (the Japanese Pharmacopoeia) (100 g) was added to the mixture with stirring, and the resultant mixture was heated in a water bath of about 60° C., so as to homogeneously dissolve the gelatin, to thereby yield gelatin composition (1).

(2) A D-sorbitol solution (the Japanese Pharmacopoeia) (150 g), concentrated glycerin (the Japanese Pharmacopoeia) (50 g), and a suitable amount of purified water were placed in a 1-liter beaker and mixed. Crystalline cellulose (the Japanese Pharmacopoeia; trade name: Avicel, product of Asahi Chemical Industry Co. Ltd.) (50 g) was added to the solution and sufficiently mixed. Subsequently, gelatin (the Japanese Pharmacopoeia) (100 g) was added to the mixture with stirring, and the resultant mixture was heated in a water bath of about 60° C., so as to homogeneously dissolve the gelatin, to thereby yield gelatin composition (2).

(3) Concentrated glycerin (the Japanese Pharmacopoeia) (80 g), sucrose (40 g), and a suitable amount of purified water were placed in a 1-liter beaker and mixed. The mixture was heated in a hot-water bath of 80° C. or higher and stirred, so as to dissolve the sucrose completely. After the solution was cooled to room temperature, polyethylene glycol 400 (40 g) and polyethylene glycol 4000 (40 g) were added to the solution and stirred to dissolve. Crystalline cellulose (the Japanese Pharmacopoeia; trade name: Avicel, product of Asahi Chemical Industry Co., Ltd.) (50 g) was further added to and dispersed in the solution. Subsequently, succinated gelatin (Japanese Patent Application No. 138457/1980) (100 g) was added with stirring and heated in a water bath of about 60° C., so that the succinated gelatin was homogeneously dissolved, to thereby yield gelatin composition (3).

(4) Concentrated glycerin (the Japanese Pharmacopoeia) (60 g), polyethylene glycol 400 (80 g), polyethylene glycol 4000 (70 g), and a suitable amount of purified water were placed in a 1-liter beaker and stirred to dissolve. Crystalline cellulose (50 g) was further added to and dissolved in the mixture with stirring. Subsequently, gelatin (the Japanese Pharmacopoeia) (100 g) was added to the mixture with stirring. The resultant mixture was heated to in a water bath of about 60° C., so as to dissolve the gelatin homogeneously, to thereby yield gelatin composition (4).

(5) Gelatin compositions (1)–(4) obtained from steps (1)–(4) above were each uniformly spread on a plastic board (80×80 cm) and dried at 25–30° C., to thereby prepare gelatin sheets having a thickness of about 0.5 mm. Each of the gelatin sheets were cut into pieces (measuring approximately 1×1 cm), and pieces corresponding to gelatin compositions (1), (2), (3), or (4) were designated gelatin sheet No. 1, No. 2, No. 3, or No. 4.

<Evaluation>

Five panelists organoleptically evaluated each gelatin sheet in terms of, among other factors, texture and stickiness of the gelatin sheets in the mouth. Also, the gelatin sheets were evaluated in terms of stickiness between sheets and between sheets and a container, under the conditions that the sheets were stored in a sealed glass vial for one month at 40° C. The results are as follows.

Gelatin sheet No. 1 (comparative product): the gelatin sheets had a soft and elastic texture, but exhibited stickiness in the mouth. The stored sheets exhibited significant adhesion to one another or to a container.

Gelatin sheet No. 2: the gelatin sheets had a soft, elastic, and pleasant chewy texture in the mouth. The sheets exhibited no stickiness in the mouth, and also had a moderate sweetness. The stored sheets exhibited no adhesion to one another or to a container, and remained as dry sheets.

Gelatin sheet No. 3: the gelatin sheets had a soft, elastic, and pleasant chewy texture. The sheets exhibited no stickiness in the mouth, moderate sweetness, and excellent solubility in the mouth. The stored sheets exhibited no adhesion to one another or to a container, and remained as dry sheets.

Gelatin sheet No. 4: the gelatin sheets had a soft, elastic, and pleasant chewy texture. The sheets exhibited no stickiness in the mouth. The stored sheets exhibited no adhesion to one another or to a container, and remained as dry sheets.

Test Example 2

The torsional rupture property of each gelatin sheet used in Test Example 1 was evaluated.

<Evaluation>

With the fingers, five panelists twisted each gelatin sheet at the corner until it was torn, and the ease of torsional tearing was evaluated. The results are shown below.

Gelatin sheet No. 1 (comparative product): The gelatin sheet was not torn even after 10 repetitions of twisting.

Gelatin sheet No. 2: The gelatin sheet was torn after 3–5 repetitions of twisting.

Gelatin sheet No. 3: The gelatin sheet was torn after 2–3 repetitions of twisting.

Gelatin sheet No. 4: The gelatin sheet was torn after 3–4 repetitions of twisting.

Comparative Example 1

Gelatin capsules each having a shell of the same composition as gelatin sheet No. 1 of Test Example 1 were prepared according to the following method.

Purified water (about 8.5 kg) and concentrated glycerin (5.0 kg) were placed in a 200-L stainless steel tank and stirred. Subsequently, gelatin (5.0 kg) was added to the mixture, followed by stirring. After the gelatin had swelled sufficiently, warm water (60–70° C.) was provided into the jacket of the stainless steel tank to thereby dissolve the gelatin. The mixture was defoamed under reduced pressure, and submitted to molding.

Molding was performed by use of a rotary-type automated molding machine. "No. 5 oval" was selected as the model capsule. After each capsule shell was filled with middle-chain fatty acid triglyceride (300 mg) and molding was carried out, the capsule was dried in a drying room at 20–25° C. so that the water content of the capsular shell became 6–10 wt. %, to thereby obtain a soft gelatin capsule No. 1 (comparative product).

Example 1

Gelatin capsule each having a shell of the same composition as gelatin sheet No. 2 of Test Example 1 were prepared according to the following method.

Purified water (about 4.5 kg), concentrated glycerin (2.5 kg), and D-sorbitol (7.5 kg) were placed in a 200-L stainless steel tank and stirred. To the solution, crystalline cellulose (Avicel PH101, product of Asahi Chemical Industry Co., Ltd.) (2.5 kg) was added and dispersed. Subsequently, gelatin (5.0 kg) was added to the mixture with stirring, and warm water (60–70° C.) was provided into the jacket of the tank to thereby dissolve the gelatin. The mixture was defoamed under reduced pressure to thereby yield a gelatin solution of interest.

Molding was conducted in the same manner as described in Comparative Example 1, except that the thus-obtained gelatin solution was used instead of the gelatin solution prepared in Comparative Example 1, to thereby yield soft gelatin capsule No. 2 (product of the present invention).

Example 2

Gelatin capsules each having a shell of the same composition as gelatin sheet No. 3 of Test Example 1 were prepared according to the following method.

Purified water (about 5.0 kg), concentrated glycerin (4.0 kg), and sucrose (2.0 kg) were placed in a 200-L stainless steel tank and mixed. Subsequently, warm water (approximately 80° C.) was provided into the jacket of the tank to thereby dissolve the sucrose with stirring. After the solution had been cooled to near room temperature with running water, polyethylene glycol 400 (2.0 kg) and polyethylene glycol 4000 (2.0 kg) were added to the solution and dissolved with stirring. Further, to the solution, crystalline cellulose (Avicel PH101, product of Asahi Chemical Industry Co., Ltd.) (2.5 kg) was dispersed. Next, succinated gelatin (Japanese Patent Application Laid-Open (kokai) No. 138457/1980) (5.0 kg) was gradually added to the mixture with stirring, and warm water (60–70° C.) was provided into the jacket of the tank to thereby dissolve the succinated gelatin. The mixture was defoamed under reduced pressure to thereby yield a gelatin solution of interest.

Molding of the capsule was conducted in the same manner as described in Comparative Example 1, except that the thus-obtained gelatin solution was used instead of the gelatin solution prepared in Comparative Example 1, to thereby yield soft gelatin capsule No. 3 (product of the present invention).

Example 3

Gelatin capsules each having a shell of the same composition as gelatin sheet No. 4 of Test Example 1 were prepared according to the following method.

Purified water (about 5.0 kg) was placed in a 200-L stainless steel tank, and concentrated glycerin (3.0 kg), polyethylene glycol 400 (4.0 kg), and polyethylene glycol 4000 (3.5 kg) were added thereto, followed by dissolution with stirring. To the solution, crystalline cellulose (Avicel PH101, product of Asahi Chemical Industry Co., Ltd.) (2.5 kg) was added with stirring and dispersed. Subsequently, gelatin (5.0 kg) was added to the mixture and stirred. Warm water (60–70° C.) was provided into the jacket of the tank in order to dissolve the gelatin, and the mixture was defoamed under reduced pressure to thereby yield a gelatin solution of interest.

Molding of the capsule was conducted in the same manner as described in Comparative Example 1, except that the thus-obtained gelatin solution was used instead of the gelatin solution prepared in Comparative Example 1, to thereby yield soft gelatin capsule No. 4 (product of the present invention).

Test Example 3

The respective soft gelatin capsules obtained in Comparative Example 1 and Examples 1–3 were organoleptically evaluated by a panel of 5 members in terms of, among other factors, texture and stickiness in the mouth. A group of fifty capsules made of each gelatin solution was tightly sealed in a glass vial, the glass vial containing the capsules was stored at 40° C. for one week, and adhesion of capsules to one another and to a container were evaluated. The results are shown below.

Soft gelatin capsule No. 1 (a comparative product): The capsule was soft and chewable but exhibited stickiness in the mouth. After storage, the capsules adhered to one another and could not be separated.

Soft gelatin capsule No. 2 (product of the present invention): The capsule was soft and chewable like the comparative product and exhibited no stickiness and easy ingestion, as well as a moderately sweet taste. After storage, the capsules exhibited no adhesion to one another and remained dry.

Soft gelatin capsule No. 3 (product of the present invention): The capsule was soft and chewable like the comparative product and exhibited no stickiness, excellent solubility, and easy ingestion, as well as a moderately sweet taste. After storage, the capsules exhibited no adhesion to one another and remained dry.

Soft gelatin capsule No. 4 (product of the present invention): The capsule was soft and chewable like the comparative product and exhibited no stickiness, excellent solubility, and easy ingestion. After storage, the capsules exhibited no adhesion to one another and remained dry.

Comparative Example 2

Soft gelatin capsule No. 5 (comparative product) was obtained in the same manner as described in Comparative Example 1, except that the capsule was made to have a form as illustrated in FIG. 1 and FIG. 2.

Example 4

Soft gelatin capsule No. 6 (product of the present invention) was obtained in the same manner as described in Comparative Example 1, except that the capsule was made to have a form as illustrated in FIG. 1 and FIG. 2.

Example 5

Soft gelatin capsule No. 7 (product of the present invention) was obtained in the same manner as described in Comparative Example 1, except that the capsule was made to have a form as illustrated in FIG. 1 and FIG. 2.

Example 6

Soft gelatin capsule No. 8 (product of the present invention) was obtained in the same manner as described in Comparative Example 1, except that the capsule was made to have a form as illustrated in FIG. 1 and FIG. 2.

Test Example 4

The respective soft gelatin capsules obtained in Comparative Example 2 and Examples 4–6 were evaluated by a panel of 5 members in terms of ease of opening when a narrow rupture portion 11 was twisted. For each gelatin solution, a group of fifty capsules was tightly sealed in a glass vial, the glass vial containing the capsules was stored at 40° C. for one week, and adhesion of capsules to one another and to a container was evaluated. The results are shown below.

Soft gelatin capsule No. 5 (comparative product): The capsule was torn after 8–10 repetitions of twisting. After storage, the capsules adhered to one another and could not be separated.

Soft gelatin capsule No. 6 (product of the present invention): The capsule was torn with 2–3 repetitions of twisting. After storage, the capsules exhibited no adhesion to one another and remained dry.

Soft gelatin capsule No. 7 (product of the present invention): The capsule was torn with 1–2 repetitions of twisting. After storage, the capsules exhibited no stickiness, and a dry feel.

Soft gelatin capsule No. 8 (product of the present invention): The capsule was torn with 2–3 repetitions of twisting. After storage, the capsules exhibited no adhesion to one another and remained dry.

The soft gelatin capsule for chewing of the present invention is easily broken in the mouth and exhibits low stickiness and excellent solubility. Therefore, the soft gelatin capsule is suitable for encapsulating, for example, pharmaceuticals, foods such as confections, and health foods.

Further, the soft gelatin capsule of the present invention is easily and reliably opened without use of any tools such as scissors by twisting with the fingers and exhibits low stickiness and excellent storage stability. Therefore, the soft gelatin capsule is especially suitable for external-use compositions and cosmetics which are removed from a capsule before use, as well as medicines which are required to be quick-acting.

Obviously, numerous modifications and variations of the present invention are possible in light of the above teachings. It is therefore to be understood that within the scope of the appended claims, the present invention may be practiced otherwise than as specifically described herein.

What is claimed is:

1. A chewable soft gelatin capsule, the capsule having a shell which comprises the following components (A), (B), and (C):
   (A) gelatin
   (B) one or more plasticizers selected from (b1)–(b3) below, in a total amount of 100–600 parts by weight based on 100 parts by weight of gelatin;
      (b1) glycerin
      (b2) a sugar selected from the group consisting of D-sorbitol, sucrose, mannitol, fructose, sugar alcohol, and isomerized sugar
      (b3) a glycol selected from the group consisting of propylene glycol and polyethylene glycol, and
   (C) a water-insoluble cellulose.

2. A chewable soft gelatin capsule according to claim 1, wherein component (B) contains glycerin (b1).

3. A chewable soft gelatin capsule according to claim 2, wherein component (B) is a combination of glycerin (b1) and at least one of sugar (b2) and glycol (b3).

4. A chewable soft gelatin capsule according to claim 2 or 3, wherein the amount of glycerin (b1) in the shell is 50–300 parts by weight with respect to 100 parts by weight of gelatin.

5. A chewable soft gelatin capsule according to claims 1, 2 or 3, wherein component (B) contains a sugar selected from among D-sorbitol, sucrose, and mannitol.

6. A chewable soft gelatin capsule according to claims 1, 2 or 3, wherein the amount of component (C) in the shell is 5–100 parts by weight with respect to 100 parts by weight of gelatin.

7. A torsional-opening soft gelatin capsule, the capsule having a shell which comprises the following components (A), (B), and (C):
   (A) gelatin
   (B) one or more plasticizers selected from (b1)–(b3) below, in a total amount of 100–600 parts by weight based on 100 parts by weight of gelatin;
      (b1) glycerin
      (b2) a sugar selected from the group consisting of D-sorbitol, sucrose, mannitol, fructose, sugar alcohol, and isomerized sugar
      (b3) a glycol selected from the group consisting of propylene glycol and polyethylene glycol, and
   (C) a water-insoluble cellulose.

8. A soft gelatin capsule of claim 7, wherein component (B) contains glycerin (b1).

9. A soft gelatin capsule of claim 8, wherein component (B) is a combination of glycerin (b1) and at least one of sugar (b2) and glycol (b3).

10. A soft gelatin capsule of claim 2 or 3, wherein the amount of glycerin (b1) in the shell is 50–300 parts by weight with respect to 100 parts by weight of gelatin.

11. A soft gelatin capsule of claims 7, 8 or 9, wherein component (B) contains a sugar selected from among D-sorbitol, sucrose, and mannitol.

12. A soft gelatin capsule of claims 7, 8 or 9, wherein the amount of component (C) in the shell is 5–100 parts by weight with respect to 100 parts by weight of gelatin.

13. A soft gelatin capsule of claims 7, 8 or 9, which has a narrow rupture portion at an arbitrary portion of the shell.

* * * * *